United States Patent [19]

Takahashi et al.

[11] Patent Number: 4,645,660

[45] Date of Patent: Feb. 24, 1987

[54] INCREASING LABELING EFFICIENCY BY FORMING DIAGNOSTIC AGENT IN THE PRESENCE OF ASCORBIC ACID OR THE LIKE

[75] Inventors: Keietsu Takahashi, Itami; Nobuo Ueda, Kawanishi; Masaaki Hazue, Amagasaki; Akira Yokoyama, Otsu; Yoshiro Ohmomo, Kyoto, all of Japan

[73] Assignee: Nihon Medi-Physics Co., Ltd., Hyogo, Japan

[21] Appl. No.: 604,261

[22] Filed: Apr. 26, 1984

[30] Foreign Application Priority Data

Apr. 26, 1983 [JP] Japan ................................. 58-73197

[51] Int. Cl.$^4$ ...................... A61K 43/00; A61K 49/00
[52] U.S. Cl. .......................................... 424/1.1; 424/9
[58] Field of Search ..................................... 424/1.1, 9

[56] References Cited

U.S. PATENT DOCUMENTS

| | | | |
|---|---|---|---|
| 4,364,920 | 12/1982 | Winchell | 424/1.1 |
| 4,425,319 | 1/1984 | Yokoyama et al. | 424/1.1 |
| 4,455,291 | 6/1984 | Tweedle | 424/1.1 |
| 4,489,053 | 12/1984 | Azuma et al. | 424/1.1 |
| 4,504,462 | 3/1985 | Van Duzee et al. | 424/1.1 |
| 4,510,125 | 4/1985 | Grogg et al. | 424/1.1 |

*Primary Examiner*—Christine M. Nucker

[57] ABSTRACT

A radioactive diagnostic agent having high labeling efficiency, prepared by bringing an aqueous solution of a radioactive metallic element contaminated with a non-radioactive metallic ions into contact with a non-radioactive carrier comprising a carrier substance having a chelate-forming property and optionally a physiologically active substance chemically bonded thereto, at least one of said aqueous solution and said non-radioactive carrier comprising at least one reductive material chosen from ascorbic acid and erythrobic acid, and their salts and esters.

8 Claims, No Drawings

INCREASING LABELING EFFICIENCY BY FORMING DIAGNOSTIC AGENT IN THE PRESENCE OF ASCORBIC ACID OR THE LIKE

The present invention relates to a radioactive diagnostic agent and its preparation. More particularly, it relates to a radioactive diagnostic agent having a high labeling efficiency and its preparation.

For the purpose of non-invading nuclear medical diagnosis such as recording, dynamic study and quantitative measurement of a blood circulation system, detection of physiological abnormality or localization of abnormality by imaging, there have been developed a variety of radioactive metallic element-labeled substances, and their clinical utility is highly valued. Those labeled substances are required to show specific accumulability at certain organs or tissues or specific behaviors corresponding to physiological states, when introduced into living bodies.

The labeled substances comprise non-radioactive carriers and radioactive metallic elements bonded thereto. Typical examples are those comprising non-radioactive carrier substances and radioactive metallic elements bonded thereto by chelate bonding. As said carrier substances, there are usually employed substances having a chelate-forming property to radioactive metallic elements and specificities to certain organs or tissues. However, their chelate forming property is frequently not sufficient. Further, the labeled substances using them are not satisfactorily stable in living bodies, and the diagnosis therewith is sometimes not reliable.

In recent years, there has been proposed to use as the carrier substances physiologically active substance-bonded chemical compounds, which comprise carrier compounds having a strong chelate-forming property and physiologically active substances having specificities to certain organs or tissues directly or indirectly bonded thereto by chemical bonding (G. E. Krejcarek: Biochemical & Biophysical Research Communication, 77, 2, 581–585 (1977); C. S. Leung, Int. J. Appl. Radiation & Isotope, 29, 687–692 (1978); Japanese Patent Publn. (unexamined) Nos. 34634/81, 125317/81, 102820/82 and 157372/82). The non-radioactive carriers in this case are thus physiologically active substance-bonded carrier compounds. Advantageously, labeled substances using such non-radioactive carriers are stable in living bodies so that the behaviors of radioactivity well coincide with those of physilogically active substances themselves. In fact, they are presently in the clinical use.

For labeling of non-radioactive carriers with radioactive metallic elements, there is usually adopted a procedure wherein non-radioactive carriers are brought into contact with radioactive metallic elements in aqueous media.

Aqueous solutions containing radioactive metallic elements to be used in the above procedure are usually contaminated with non-radioactive metallic ions as the impurity. For instance, aqueous solutions containing gallium-67 or indium-111 produced by the use of a cyclotron contain ferric ion, cupric ion, etc. in concentrations of several ppm. Further, for instance, commercially available inorganic acids to be used for purification of radioactive metallic elements contain ordinarily iron ion in the order of ppm. On the other hand, the normal radioactivitiy of a radioactive metallic element for the clinical use is around 1 mCi, which corresponds to the order of several ng. Accordingly, the concentration of a radioactive metallic element is usually so small as about 1/1000 of that of the non-radioactive metallic ions as the impurity.

When the non-radioactive carrier is contacted with such aqueous solution of the radioactive metallic element having a high content level of non-radioactive metallic ions, the chelate bonding of the radioactive metallic element to the non-radioactive carrier is competitive with that of the non-radioactive metallic ions so that the labeling efficiency of the radioactive metallic element will be much lowered.

In order to enhance the labeling efficiency, consideration has been given to use of the non-radioactive carrier in an amount greatly in excess of the non-radioactive metallic ions. However, this is not favorable, because toxicity or antigenic property due to the non-radioactive carrier may be produced. Alternatively, when the non-radioactive carrier is the physiologically active substance-bonded carrier compound, the increase of the molecules of the carrier compound to be bonded to each molecule of the physiologically active substance is considered, but this may deteriorate the physiological activity of the physiologically active substance so as to lower the accuracy of diagnosis.

As a result of the extensive study, it has now been found that the use of a certain reductive substance can assure a high labeling efficiency of the non-radioactive carrier with a radioactive metallic element. This invention is based on the above finding.

According to the present invention, there is provided a radioactive diagnostic agent of high labeling efficiency which comprises a non-radioactive carrier having a chelate-forming property and a radioactive metallic element bonded thereto by chelate bonding, and a reductive material chosen from ascorbic acid and erythorbic acid, and their salts and esters in an aqueous medium. There is also provided a kit for preparation of said radioactive diagnostic agent which comprises (1) a non-radioactive carrier having a chelate-forming property and (2) an aqueous solution comprising a radioactive metallic element, at least one of said non-radioactive carrier and said aqueous solution containing a reductive material chosen from ascorbic acid and erythorbic acid, and their salts and esters. There is further provided a method for preparation of said radioactive diagnostic agent which comprises bringing a non-radioactive carrier having a chelate-forming property into contact with an aqueous solution comprising a radioactive metallic element, at least one of said non-radioactive carrier and said aqueous solution containing a reductive material chosen from ascorbic acid and erythorbic acid, and their salts and esters.

The reason why the presence of the reductive material assures a high labeling efficiency is not clarified yet; but it is assumed that the reductive material acts predominantly on the non-radioactive metallic ions so as to lower their chelate-forming property.

As the reductive material, there may be used any one chosen from ascorbic acid and erythorbic acid, and their salts and esters, which are pharmaceutically acceptable. In general, they are quite less toxic to living bodies. Most of them, particularly ascorbic acid and erythorbic acid, are commercially available. They are preferred to be easily soluble in water, more specifically an aqueous solution containing a radioactive metallic element. The salts and esters may be prepared from ascorbic acid or erythorbic acid by neutralization or esterification according to a conventional procedure. Examples of the salts are alkali metal salts (e.g. sodium salt, potassium salt), alkaline earth metal salts (e.g. calcium salt, barium salt), heavy metal salts (e.g. iron salt, manganese salt), ammonium salts, etc. Examples of the esters are lower alkyl esters (e.g. methyl ester, ethyl ester, propyl ester, isopropyl ester, butyl ester), ar(lower)alkyl esters (e.g. benzyl ester, phenethyl ester), etc.

The amount of the reductive material to be used may be appropriately determined on the content of the non-radioactive metallic ions in the aqueous solution of the radioactive metallic element. It should be sufficient to reduce the contaminating non-radioactive metallic ions so as to assure a high radioactivity as well as a high labeling efficiency but not so great to exert a material toxicity. In general, the reductive material may be used in an amount of 0.001 to 10 mM, particularly of 0.01 to 3 mM per 1 ml of the aqueous radioactive metallic element solution.

The reductive material may be incorporated in the non-radioactive carrier. The non-radioactive carrier may be formulated in a powder form (lyophilized or not) or in an aqueous solution form. Further, such formulation may comprise additionally any conventional additive such as a pH regulating agent (e.g. an acid, a base), an isotonizing agent (e.g. sodium chloride), a preservative (e.g. benzyl alcohol), etc.

Additionally or alternatively, the reductive material may be incorporated in the aqueous radioactive metallic element solution.

The non-radioactive carrier to be used in the invention comprises any substance which has a chelate-forming property and a specificity to any organ or tissue in a living body. Usually, such substance is per se physiologically active but relatively weak in chelate-forming property. Therefore, a chemical compound having any reactive functional group in addition to a chelate-forming property may be chemically combined with any other substance having a specificity to any organ or tissue to obtain a carrier substance having a chelate-forming property. Usually and preferably, this latter substance has a physiological activity.

When the non-radioactive carrier comprises a carrier substance having itself a chelate-forming property as well as a specificity to an organ or tissue, it may be, for instance, diethylenetriamine pentaacetic acid, ethylenediamine triacetic acid, ethylenediamine diacetic acid, propylenediamine diacetic acid, citric acid, bleomycin, etc.

When the non-radioactive carrier comprises a carrier compound and a physiologically active substance bonded thereto by chemical bonding, it may be produced by reacting the physiologically active substance directly or indirectly with the carrier compound by a conventional procedure. As the carrier compound, there may be used any compound which is capable of reacting chemically with a physiologically active substance without causing any material change of the physiological activity of the latter and has a chelate-forming property with a radioactive metallic element. Examples of the carrier compound are diethylenetriamine pentaacetic acid, ethylenediamine triacetic acid, 3-oxobutyral-bis(N-methylthiosemicarbazone)carboxylic acid, deferoxamine, 3-aminomethylene-2,4-pentanedione-bis(thiosemicarbazone) derivative, 1-(p-aminoalkyl)phenyl-propane-1,2-dione-bis(N-methylthiosemicarbazone) derivatives, etc. The reaction procedure between the carrier compound and the physiologically active substance may be carried out by a conventional procedure, for instance, as diclosed in U.S. Pat. Nos. 4,287,362, 4,338,248, 4,425,319 and 4,440,739.

As the radioactive metallic element, there are exemplified radioactive metallic elements as conventionally employed. Specific examples are gallium-67, gallium-68, indium-111, indium-113m, thallium-201, cobalt 55, etc.

The radioactive diagnostic agent of this invention may be administered to patients in an amount sufficient to produce the radioactivity necessary for examination of the organ or tissue by an appropriate route, usually through an intravenous route. For instance, the intravenous administration of the radioactive diagnostic agent of about 1 to 3 ml in volume having a radioactivity of about 0.5 to 20 mCi, particularly of about 1 to 10 mCi, to a patient is quite suitable for the diagnostic purpose.

Practical and presently preferred embodiments of the invention are illustratively shown in the followng examples.

EXAMPLE 1

Preparation of a non-radioactive carrier:

Deferoxamine (26 mg) was dissolved in 0.01M phosphate buffer-0.15M sodium chloride solution (hereinafter referred to as "PBS"), a 25% aqueous solution of glutaraldehyde was added thereto to make an equimolar concentration of glutaraldehyde to deferoxamine, and the resultant mixture was agitated at room temperature for about 10 minutes to make a solution (A).

Separately, fibrinogen (500 mg) was dissolved in PBS (40 ml) to make a solution (B). The solution (A) was added to the solution (B) at 0° to 4° C., and stirring was continued at the same temperature as above for about 1 hour. To the resultant mixture, sodium borohydride (10 mg) was added, followed by stirring at 0° to 4° C. in about 1 hour so as to perfect the reduction.

The reaction mixture was subjected to column chromatography on Sephadex G-50 (4.4×50 cm) using PBS as an eluting solution for elimination of unreacted materials, etc. The resulting solution containing a fibrinogen-deferoxamine reduction product was adjusted to make a concentration of 5.0 mg/ml, and sodium L-ascorbate was added thereto so as to make a concentration of 30 mM, 50 mM or 100 mM. One milliliter of the resultant solution was filled in a vial to make a non-radioactive carrier.

The above operation was carried out under sterile conditions.

EXAMPLE 2

Preparation of a radioactive diagnostic agent:

To the non-radioactive carrier as obtained in Example 1, an aqueous solution containing gallium-67 in the form of gallium chloride (1 ml; 0.5 mCi) was added to make a radioactive diagnostic agent as a pale yellow, transparent solution having a pH of about 7.4.

EXAMPLE 3

Labeling efficiency of a radioactive diagnostic agent:

The radioactive diagnostic agent as prepared in Example 2 was subjected to electrophoresis using a veronal buffer (pH 8.6) as a developing solution and a cellulose acetate membrane as a electrophoretic membrane with an electric current of 1.7 mA/cm for 15 minutes. Scanning was effected by the use of a radiochromatoscanner to examine the variation of the labeling efficiency depending upon the concentration of sodium L-ascorbate contained in the radioactive diagnostic agent. The test results are shown in Table 1.

TABLE 1

Labeling efficiency of the radioactive diagnostic agent 60 minutes after the preparation

| Concentration of sodium L-ascorbate (mM) | Labeling efficiency (%) |
|---|---|
| 0 | 70.3 |
| 30 | 85.2 |
| 50 | 89.1 |
| 100 | 98.3 |

As understood from the above results, the labeling efficiency was increased with the increase of the concentration of sodium L-ascorbate. At sixty minutes after the preparation, the labeling rate in the system not containing sodium L-ascorbate was 70.3%, while that in the system containing sodium L-ascorbate (100 mM) was 98.3%; the specific radioactivity in the system not containing sodium L-ascorbate was 0.07 mCi/mg, while that in the system containing sodium L-ascorbate was 0.1 mCi/mg. Thus, the incorporation of sodium L-ascorbate into the system of a radioactive diagnostic agent can afford higher labeling rate and specific radioactivity.

When sodium L-ascorbate is not contained, the system contains free gallium-67 in a content of 30%, which is not suitable for the purpose of nuclear medical diagnosis. The preparation containing 100 mM sodium L-ascorbate shows a high labelling efficiency and is practically usable.

EXAMPLE 4

Preparation of a non-radioactive carrier:

Deferoxamine was dissolved in PBS (pH 7.4) to make a concentration of $1.2 \times 10^{-4}$ mol/ml. A 25% aqueous solution of glutaraldehyde was added thereto to make an equimolar concentration of glutaraldehyde to deferoxamine. After 10 minutes, the mixture was stirred at room temperature to give a solution (A).

Separately, human serum albumin (lyophilized; 266 mg) was dissolved in PBS (20 ml) to give a solution (B). The solution (B) was admixed with the solution (A) (0.3 ml) at 0° to 4° C., and stirring was continued at the same temperature as above for about 1 hour. Sodium borohydride (5 mg) was added to the resultant mixture and stirring was further continued at 0° to 4° C. for about 1 hour, whereby reduction proceeded.

The reaction mixture was subjected to column chromatography on Sephadex G-50 (5×20 cm) using PBS as an eluting solution for elimination of unreacted materials, etc. The resulting solution containing human serum albumin-deferoxamine reduction product was adjusted to make a concentration of 5.0 mg/ml, and sodium L-ascorbate was added thereto so as to make a concentration of 100 mM. One milliliter of the resultant solution was filled in a vial to make a non-radioactive carrier.

All the above operations were effected under sterile conditions.

EXAMPLE 5

Preparation of a radioactive diagnostic agent:

A 0.01M hydrochloric acid solution (1 ml) containing $^{67}$Ga (1 mCi) in the form of gallium chloride was added to a solution containing the human serum albumin-deferoxamine reduction product as prepared in Example 4 (2 ml) to give a radioactive diagnostic agent as a pale yellow clear solution (pH 7.0).

EXAMPLE 6

Preparation of a non-radioactive carrier:

Human serum albumin was dissolved in 0.1M sodium hydrogen carbonate buffer (pH 8.2) to make a concentration of 20 mg/ml. Diethylenetriamine pentaacetic anhydride was added thereto in an amount of 8 moles per 1 mole of human serum albumin, and the resultant mixture was stirred at room temperature for about 1 hour. The reaction mixture was subjected to Sephacryl S-200 (2.2×75 cm) and eluted with 0.05M sodium chloride solution to give an aqueous solution containing human serum albumin-diethylenetriamine pentaacetic acid, which was then adjusted to make a concentration of human serum albumin of 1 mg/ml. Sodium L-ascorbate was added thereto to make a concentration of 30 mM, whereby a non-radioactive carrier was obtained. Each one milliliter of the above aqueous solution was filled in a vial.

All the above operations were effected under sterile conditions.

EXAMPLE 7

Preparation of a radioactive diagnostic agent:

To 1 ml of the non-radioactive carrier as obtained in Example 6, an aqueous solution of indium-111 (2.0 mCi) in the form of indium chloride (1 ml) was added to make a radioactive diagnostic agent (pH about 5.2).

EXAMPLE 8

Preparation of a non-radioactive carrier:

Fibrinogen was dissolved in 0.1M sodium hydrogen carbonate buffer (pH 8.2) to make a concentration of 10 mg/ml. Diethylenetriamine pentaacetic anhydride was added thereto in an amount of 8 moles per 1 mole of fibrinogen, and the resultant mixture was stirred at room temperature for about 1 hour. The reaction mixture was subjected to Sepharose CL-6B (2.2×75 cm) and eluted with 0.05M phosphate buffer (pH 6.5) to give an aqueous solution containing fibrinogen-diethylenetriamine pentaacetic acid, which was then adjusted to make a concentration of fibrinogen of 2 mg/ml. Sodium L-ascorbate was added thereto to make a concentration of 50 mM, whereby a non-radioactive carrier was obtained. Each one milliliter of the above aqueous solution was filled in a vial.

All the above operations were effected under sterile conditions.

EXAMPLE 9

Preparation of a radioactive diagnostic agent:

To 1 ml of the non-radioactive carrier as obtained in Example 7, an aqueous solution of indium-111 (2.0 mCi) in the form of indium chloride (1 ml) was added to make a radioactive diagnostic agent (pH about 6.5).

EXAMPLE 10

Preparation of a non-radioactive carrier:

Diethylenetriamine pentaacetic acid was dissolved in distilled water to make a concentration of 0.2 mg/ml. Sodium L-ascorbate was added thereto to make a concentration of 10 mM, followed by adjusting the pH to 7.5. Each one milliliter of the resultant solution was filled in a vial.

All the above operations were effected under sterile conditions.

EXAMPLE 11

Preparation of a radioactive diagnostic agent:

To 1 ml of the non-radioactive carrier as obtained in Example 10, an aqueous solution of indium-111 (2.0 mCi) in the form of indium chloride (1 ml) was added to make a radioactive diagnostic agent (pH about 7.5).

What is claimed is:

1. A method for enhancing the labeling efficiency of a non-radioactive carrier with a radioactive metallic element other than technetium-99m in the presence of a non-radioactive metallic element as an impurity, said non-radioactive carrier comprising deferoxamine or its combined product with a physiologically active substance, said method comprising the step of contacting the non-radioactive carrier with the radioactive metallic element in the presence of a non-toxic amount of a reductive material selected from the group consisting of ascorbic acid, erythorbic acid, and their salts and esters.

2. A method as recited in claim 1 wherein the non-radioactive carrier comprises deferoxamine chemically combined with a physiologically active substance.

3. A method as recited in claim 2 wherein the physiologically active substance is fibrinogen.

4. A method as recited in claim 3 wherein the non-radioactive carrier is brought into contact with an aqueous solution comprising the radioactive metallic element with non-radioactive metallic ions as impurity, at least one of said non-radioactive carrier or said aqueous solution being in combination with said reductive material.

5. A method as recited in claim 2 wherein the non-radioactive carrier is brought into contact with an aqueous solution comprising the radioactive metallic element with non-radioactive metallic ions as impurity, at least one of said non-radioactive carrier or said aqueous solution being in combination with said reductive material.

6. A method as recited in claim 5 wherein said non-radioactive carrier is in combination with said reductive material when said carrier is brought into contact with said aqueous solution comprising radioactive metallic element.

7. A method as recited in claim 6 wherein the amount of reductive material is sufficient to reduce the contaminating non-radioactive metallic ions so as to assure a high radioactivity as well as high labeling efficiency.

8. A method as recited in claim 1 wherein the radioactive metallic element is selected from the group consisting of gallium-67, gallium-68, indium-111, indium-113m, thallium-201, and cobalt-55.

* * * * *